US007076023B2

(12) United States Patent
Ghelmansarai et al.

(10) Patent No.: US 7,076,023 B2
(45) Date of Patent: Jul. 11, 2006

(54) X-RAY THERAPY ELECTRONIC PORTAL IMAGING SYSTEM AND METHOD FOR ARTIFACT REDUCTION

(75) Inventors: Farhad Abbasi Ghelmansarai, Danville, CA (US); William F. Collins, Clayton, CA (US)

(73) Assignee: Siemens Medical Solutions USA, Inc., Iselin, NJ (US)

( * ) Notice: Subject to any disclaimer, the term of this patent is extended or adjusted under 35 U.S.C. 154(b) by 0 days.

(21) Appl. No.: 10/039,607

(22) Filed: Oct. 26, 2001

(65) Prior Publication Data

US 2003/0083564 A1 May 1, 2003

(51) Int. Cl.
*A61N 5/10* (2006.01)

(52) U.S. Cl. .......................... 378/65; 378/98.8
(58) Field of Classification Search ............... 378/65, 378/98.8; 250/370.09
See application file for complete search history.

(56) References Cited

U.S. PATENT DOCUMENTS 6,307,915 B1 * 10/2001 Frojdh ....................... 378/98.8
6,487,274 B1 * 11/2002 Bertsche ..................... 378/143

OTHER PUBLICATIONS

"Megavoltage Cone–Beam Computed Tomography Using a High–Efficiency Image Receptor," by Ed J. Seppi et al. Ginzton Technology Center, Varian Medical Systems, Mountain View, CA; Int. J. Radiation Oncology Biol. Phys., vol. 55, No. 3, p. 793–803; 2003 pub aft filing date.

"Introduction of a Novel Dose Saving Acquisition Mode for the Portal Vision™ aS560 EPID to Facilitate On–Line Patient Setup Verification," by D Vetterli et al.; Med. Phys. 31 (4), Apr. 2004; 2004 Am. Assoc. Phys. Med; pgs. 828–831 published after filing date.

"Preclinical Studies of Megavoltage Cone Beam CT Systems for Tumor Localization in Gated Radiotherapy of Lung Cancer," by Gig S. Mageras et al.; Department of Medical Physics, Memorial Sloan–Kettering Cancer Center, New York, NY, USA and Ginzton Technology Center, Varian Medical Systems, Mountain View, GA; XIVth ICCR; May 10–13, 2004 Seoul, Korea published after filing date.

* cited by examiner

*Primary Examiner*—Craig E. Church

(57) ABSTRACT

X-ray therapy EPI artifact reduction and control of imaging is provided. Scanning of images is synchronized with the pulse rate of the x-rays. The scanning period is longer than the pulse rate period, so artifacts are generated within the resulting images. Due to the synchronization, the pulse variation artifacts are aligned across multiple images. The synchronization and resulting alignment of linear artifacts allows for gain correction as a function of lines within the image. Such gain correction reduces or removes non-linearities associated with pulse rate variation.

14 Claims, 3 Drawing Sheets

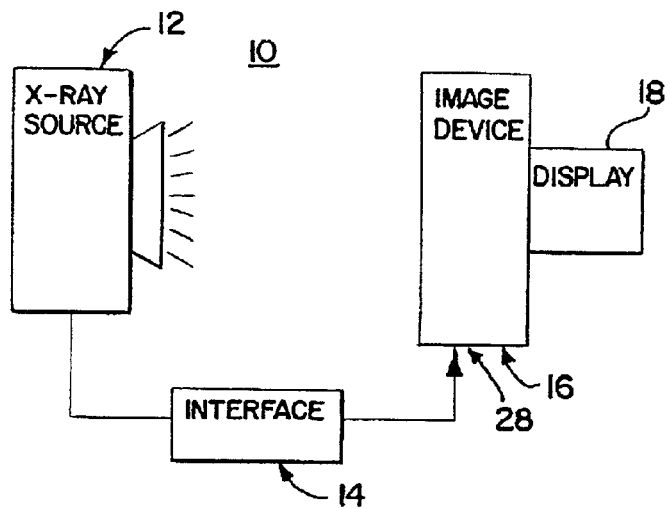
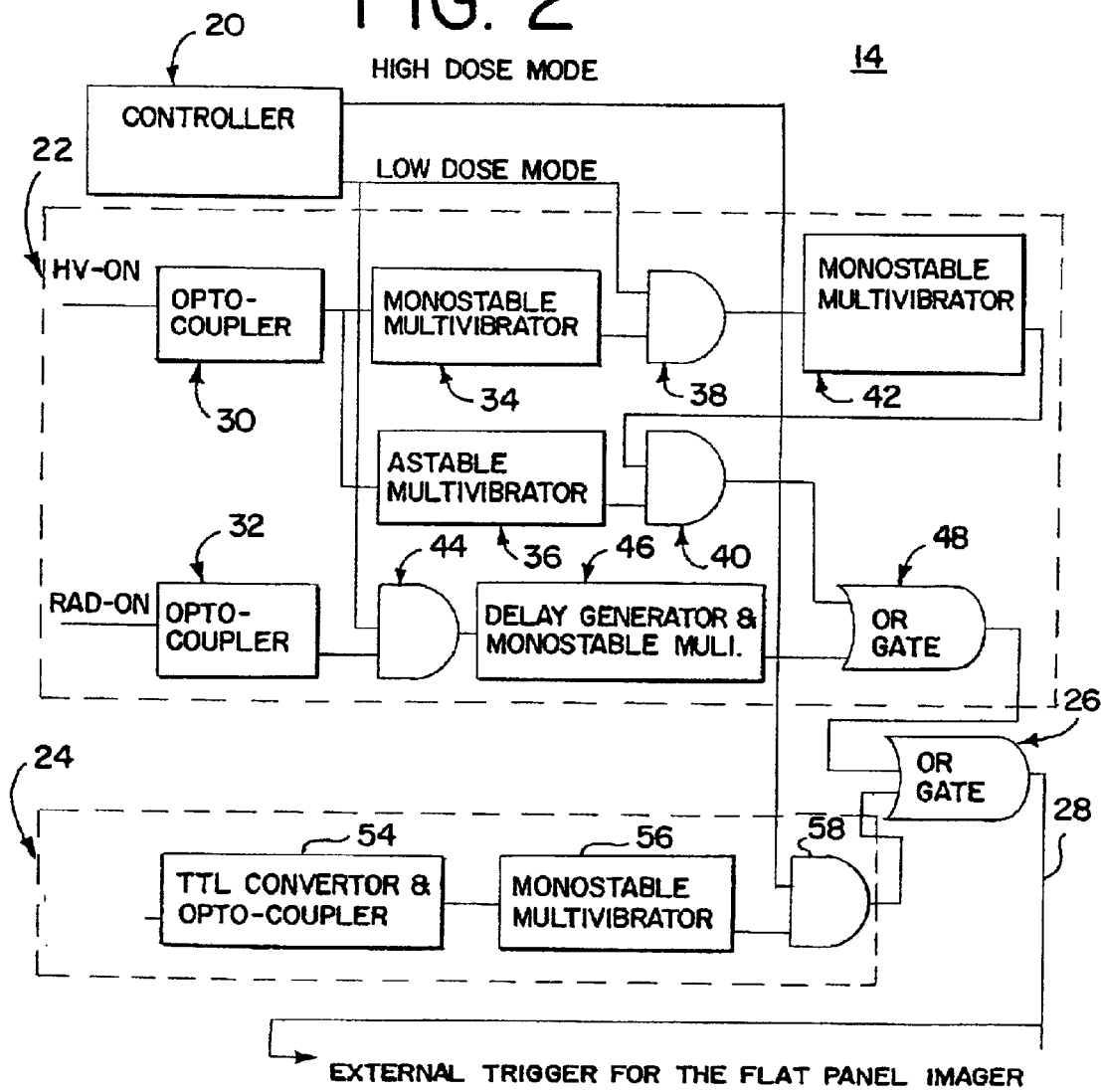

X-RAY THERAPY ELECTRONIC PORTAL IMAGING SYSTEM AND METHOD FOR ARTIFACT REDUCTION

BACKGROUND

The present invention relates to x-ray imaging and dosimetric measurements. In particular, reduction of linear accelerator pulsing artifacts for electronic imaging devices of x-rays are provided.

X-ray treatment uses the therapeutic application of x-ray energy to destroy tumor tissue or for other therapy. X-rays generated by a megavoltage or other high voltage sources generate x-ray pulses or periodically vary the amplitude of the x-rays output, such as every 5 milliseconds.

X-ray imaging detectors output signals responsive to the incident x-rays. The variation in the x-rays results in image artifacts. Where multiple images are combined or averaged, the pulse rate variation artifacts are randomly averaged or combined. The resulting combined image also undesirably includes artifacts.

X-ray images generated digitally are used for dosimetric treatment verification. The pulse rate variation artifacts introduce a non-linearity within the images. The artifacts adversely affect measurement and image diagnosis of x-ray therapy.

BRIEF SUMMARY

The present invention is defined by the following claims, and nothing in this section should be taken as a limitation on those claims. By way of introduction, the preferred embodiments described below include methods and systems for x-ray therapy with reduced pulse rate artifacts variations or removal of x-ray pulsing effects from EPI. Scanning of images is synchronized with the pulse rate of the x-rays. The scanning period is longer than the pulse rate period, so intensity artifacts are generated within the resulting images. Using the synchronization, the pulse variation artifacts are aligned across multiple images. The synchronization and resulting alignment of linear artifacts allows for gain correction as a function of lines within the image. Such gain correction reduces or removes non-linearities associated with pulse rate variation.

In one aspect, a dosimetric therapy system for artifact reduction is provided. An x-ray source has an output responsive to an x-ray pulse rate. An imaging device is responsive to x-rays from the x-ray source. The imaging device has a scan trigger input connected with the output of the x-ray source.

In a second aspect, an interface system is provided for synchronizing an electronic x-ray imaging device with pulses of an x-ray machine. A low dose circuit responsive to an x-ray source high voltage power-on signal and a radiation off signal is operable to generate a first trigger signal and a second trigger signal. The first trigger signal is responsive to the x-ray source high voltage power-on signal, and the second trigger signal is responsive to the radiation-off signal. A high dose circuit is operable to generate a third trigger signal synchronized with an x-ray pulse signal.

In a third aspect, an interface system for synchronizing an electronic x-ray imaging device with pulses of an electronic x-ray machine is provided. An input connects with a trigger circuit. An output also connects with the trigger circuit. An output signal responsive to a periodic input signal on the input is provided on the output.

In a fourth aspect, a method for artifact reduction in x-ray therapy systems is provided. A sequence of x-ray pulses are generated. Imaging is performed in response to the x-ray pulses during generation of the x-ray pulses. The imaging is synchronized with the x-ray pulses.

In a fifth aspect, a method for artifact reduction in dosimetric therapy systems is provided. An image with linear pulse artifacts is generated. The image is gained corrected as a function of a line.

Further aspects and advantages of the invention are discussed below in conjunction with the preferred embodiments.

BRIEF DESCRIPTION OF SEVERAL VIEWS OF THE DRAWINGS

The components and the figures are not necessarily to scale, emphasis instead being placed upon illustrating the principles of the invention. Moreover, in the figures like reference numerals designate corresponding parts throughout the different views.

FIG. 1 is a block diagram of one embodiment of an x-ray therapy system.

FIG. 2 is a block circuit diagram of an interface system of one embodiment for synchronizing an electronic x-ray imaging device with an x-ray machine.

DETAILED DESCRIPTION OF THE PREFERRED EMBODIMENTS

Figure 3:
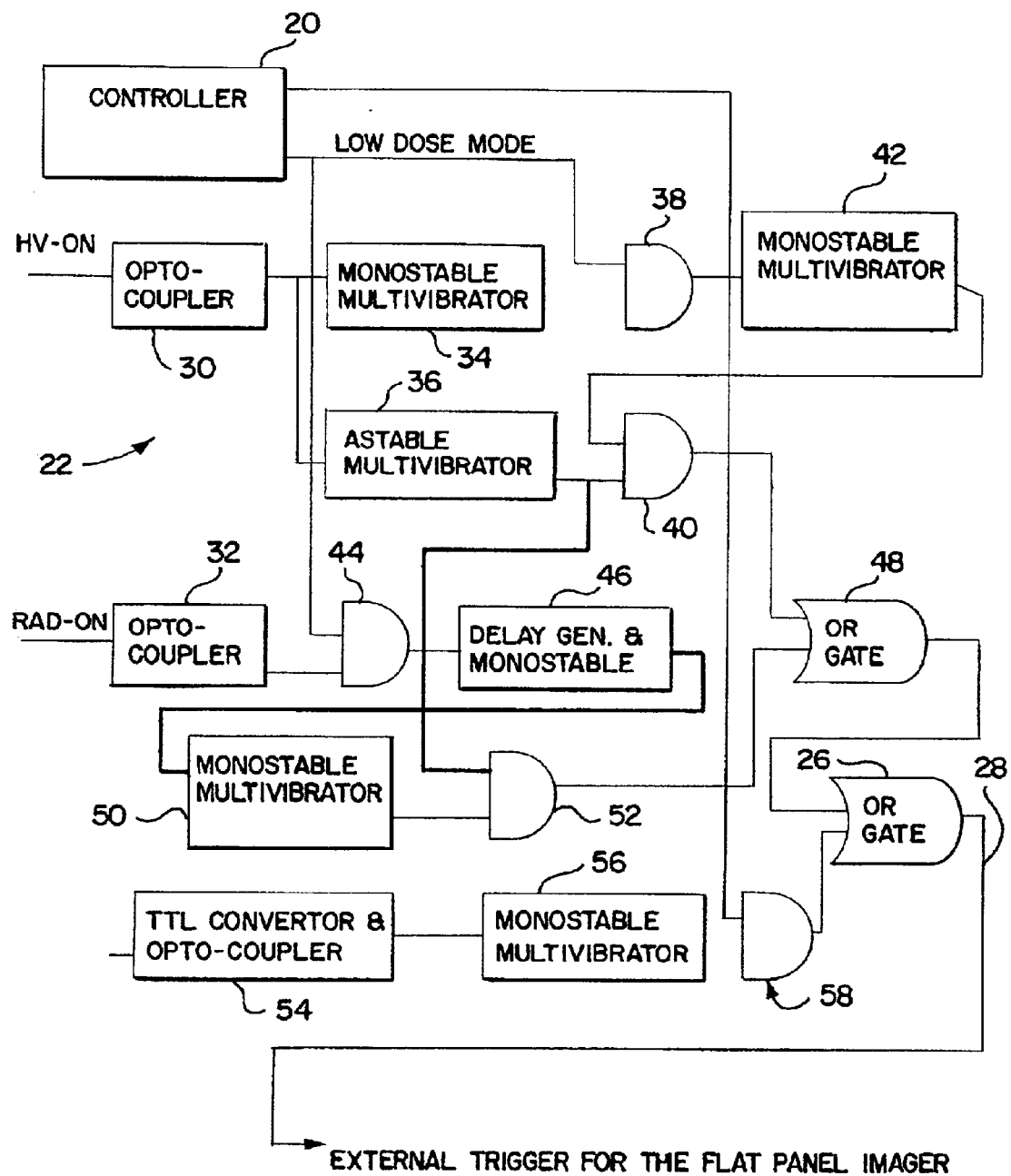
FIG. 3 is an alternative embodiment of a block circuit diagram for synchronizing an electronic x-ray imaging device with an x-ray machine.

Image scans of a digital x-ray imaging device are synchronized with pulses of x-rays from an x-ray source. Synchronization aligns the resulting pulsing artifacts within multiple images. Location of the artifacts is known, and the combination of multiple images results in distinct artifact patterns. The artifacts are associated with linear positions within the images, such as horizontal lines across images. By controlling gain as a function of line, the x-ray pulse variation artifacts are removed or reduced. Electronic readouts provide information for stable, accurate dosimetric measurements.

FIG. 1 shows an x-ray therapy system 10 of one embodiment. The x-ray therapy system 10 includes an x-ray source 12, and interface 14, and an imaging device 16 with a display 18. Additional components, such as a patient bed, motors, components for Intensity Modulation Radio Therapy (IMRT) or other therapeutic x-ray components, may be included. In alternative embodiments, the interface 14 comprises part of the x-ray source 12 or the imaging device 16. In one embodiment, the x-ray therapy system 10 comprises a PRIMUS® system with digital imaging capabilities from Siemens Medical Systems. X-ray therapy systems from other manufacturers may be used.

The x-ray source 12 comprises a megavoltage or other voltage linear accelerator for generating x-rays for medical treatment. Depending on the intended medical therapy, lower energy, mid-energy or high energy linear accelerators may be used. The x-ray source 12 has a fixed position or is operable to be moved through multiple positions, such as associated with IMRT. Additional features may be provided for the x-ray source 12, such as combination with CT scanners, combination with other imaging devices, multileaf collimators, or other systems or devices.

The x-ray source 12 outputs x-rays at a selectable energy level for medical imaging and therapy treatment. The x-ray source 12 also outputs data or information signals representing operation of the x-ray source. In one embodiment, a high voltage power-on signal, a radiation-on and off signal, and a radiation or x-ray pulse signal are output. The high voltage power-on signal indicates that the x-ray source 12 is powered on or switched on for application of x-rays. The radiation-on and off signal indicates that x-rays are being generated or not generated by the x-ray source 12. The x-ray pulse signal indicates the pulse rate or period for variable generation of x-rays. For example, when the radiation is on, a pulse signal is provided every 5 milliseconds corresponding to the x-rays pulsing off at 5 millisecond intervals. The pulse rate information is provided in synchronization with actual pulsing of the x-ray source 12.

In alternative embodiments, different, additional, or fewer output information signals are provided. For example, the radiation on and off signal is multiplexed with or includes the pulse rate information. As yet another example, data indicating a pulse rate or period for use by a timer is provided prior to turning-on the radiation.

The imaging device 16 is synchronized with the x-ray source 12. The imaging device 16 comprises an Electronic Portal Imaging Device (EPID) or other large area flat panel digital x-ray imaging detector for radiographic application. For example, a Beamview® EPID imaging system from Siemens Medical Systems is used, but imaging devices from other manufacturers may be provided. In one embodiment, a two-dimensional scintillator or phosphor screen converts x-rays to light. A two-dimensional active matrix of photodetectors or thin film transistors made of amorphous or polycrystalline silicon or other semiconductor materials converts the light energy into electrical energy. Readout electronics of the active matrix scan the photodiodes to acquire electrical imaging data. The amount of electric charge generated by the photodiodes or other x-ray detectors is linearly related to the amount of radiation or the photon count received at the imaging device 16. Each scan or readout from the two-dimensional array of the active matrix provides an associated plurality of pixel information representing a two-dimensional area. The information represents the sum of or total amount of radiation provided at locations on the two-dimensional array since a previous readout cleared or reset the stored electric charges.

The image information is stored and processed to provide a per pixel indication of radiation dosage at each received pixel. One or more processors, application specific integrated circuits, logic devices or analog circuits controls the scanning, storing and processing of the image information. For example, a control processor causes a plurality of frames or scans of image information to be combined to form a single image, such as averaging or summing a plurality of frames of information associated with a single or multiple therapeutic dosages of x-rays. As another example, the processor applies offset correction to account for dark current or bias currents of the transistors or active matrix, mean or pixel correction to allow for software correction of defective pixels, and gain correction to homogenize different pixel sensitivities. In one embodiment, gain correction is applied as a function of line relative to the two-dimensional imaging array. For example, data representing a line within the two-dimensional region is increased or decreased relative to other lines of data for removing or reducing artifacts from pulse rate variations or linear accelerator pulsing effects. In alternative embodiments, dedicated hardware or separate processors perform any one or more of the various imaging processing functions described above or other imaging processes.

The display 18 of the imaging device 16 is a flat panel or CRT monitor. Projection, photographic or other displays may be used in alternative embodiments. The display 18 generates an image based on the image data acquired by the imaging device.

The imaging device 16 also includes an external scan trigger input 28. The imaging device 16 scans or generates image data in response to a trigger signal applied to the external scan trigger input 28. Additionally or alternatively, the imaging device 16 scans the active matrix as a function of internal triggers, such as timing signals.

The imaging device 16 is synchronized with the pulse rate of the x-ray source 12 by connecting the pulse signal with the external scan trigger input of the imaging device 16. The pulse indications trigger imaging by the imaging device 16. Alternatively, data is input to the imaging device 16 indicating a start of radiation, and expected timing of pulses or a pulse period data provide synchronization information.

In one embodiment, the interface device 14 converts signals output by the x-ray source 12 into a format usable by the imaging device 16 at the external scan trigger input. Additionally or alternatively, the interface 14 provides additional control for triggering image scanning. In yet other alternative embodiments, a signal output by the x-ray source 12 is connected directly to the scan trigger input 28 of the imaging device 16.

FIG. 2 shows an interface 14 of one embodiment. The interface 14 includes a controller 20, a low dosage circuit 22, a high dosage circuit 24, an OR gate 26 and the trigger output 28. In alternative embodiments, additional, different or fewer components may be included. For example, only the high dose circuit 24 is provided.

The controller 20 comprises a transistor, a switch, a processor, logic device, analog device, software switch or other device for controlling or selecting the low or high dose circuits 22, 24. The controller 20 determines a mode of operation of the interface 14. The controller 20 switches between the high dose mode and the low dose mode. For example, the controller 20 selects between generation of trigger signals for low or high dosage readout or triggering. For low dose trigger generation, trigger signals are generated for patient localization imaging, such as to establish the appropriate positioning of a patient relative to the x-ray source 12. The high dose mode provides trigger signals for substantially continuous scanning. The trigger signals are synchronized with the pulse rate signals from the x-ray source 12. After each trigger signal is generated, other pulse signals from the x-ray source do not trigger until the end of the frame (i.e. a selected frame has been scanned or a particular frame period has elapsed). Trigger signals during the frame scan period are ignored by the imaging device 16. Subsequently, another trigger signal is generated in synchronization with another pulse signal from the x-ray source 12. The controller 20 is responsive to user selection or indication of the operation of the x-ray source 12, such as selection of positioning imaging or therapeutic imaging.

In alternative embodiments, additional control, such as timing adjustment or other control is provided by the controller 20. In yet other alternative embodiments, the controller 20 controls one, or three or more trigger generation circuits.

The OR gate 26 passes trigger signals from either of the low dose circuit 22 or the high dose circuit 24. In alternative embodiments, the trigger signals from the low and high dose circuits 22, 24 are provided separately to the imaging device 16 or are combined by connection of signal lines or other logic circuits.

The low dose circuit 22 synchronizes the imaging device 16 with the x-ray source 12. The low dose circuit 22 comprises a pair of opto couplers 30, 32, monostable multi-vibrators 34, 42, astable multi-vibrator 36, delay generator and monostable multi-vibrator 46, AND gates 38, 40, and 44 and an OR gate 48. Additional, different or fewer components may be provided. The low dose circuit 22 generates trigger signals to refresh the imaging device 16 and to trigger generation of an image scanned after application of x-ray radiation has ended.

The opto-couplers 30 and 32 isolate the low dose circuit 22 from the x-ray source 12 for receiving a high voltage power-on signal and the radiation on/off signal. Three multi-vibrators 34, 36, 42 and two AND gates 38, 40 generate a trigger signal for refreshing or clearing the imaging device 16 (FIG. 1) in preparation for imaging from x-rays. The two monostable multi-vibrators 34, 42 generate a high or low signal for a particular time period in response to a high or low or changing input voltage. Accordingly, the monostable multi-vibrators 34, 42 act as pulse width circuits or circuits for generating a timing or pulse signal. Other pulse circuits with or without multi-vibrators may be used.

In response to the high voltage being powered on, the monostable multi-vibrator 34 switches to a different output, such as switching to a high output, for one millisecond or other time period. The astable multi-vibrator 36 generates a square waveform or other periodic waveform. In one embodiment, the square waveform has a 350 millisecond period, such as the same as or greater than a scan rate of the imaging device 16.

The AND gate 38 receives the output of the monostable multi-vibrator 34 The multi-vibrators of the interface 14 comprise latches or other logic circuits and associated resistors, variable resistors, capacitors and inductors form controlling the timing of operation of the latch circuit. and the control signal from the controller 20. The control signal enables operation of the low dose circuit. If the interface 14 is operating in the low dose mode and the monostable multi-vibrator output 34 is switched high, the AND gate 38 outputs a high signal to the monostable multi-vibrator 42.

The monostable multi-vibrator 42 switches to or latches a high output for 1600 milliseconds or other amount of time for a refresh time. The next AND gate 40 receives the signal from the refresh time monostable multi-vibrator 42 and the astable multi-vibrator 36. The monostable multi-vibrator 42 enables the AND gate 40 for output during the refresh time. The output of the astable multi-vibrator 36 generates periodic trigger signals while the AND gate 40 is enabled for refreshing the imaging device 16 a plurality of times during the refresh period. Given the 1,600 millisecond refresh period and the astable multi-vibrator 350 millisecond cycle, four refresh scan triggers are generated. The refresh period is a function of the difference in time between the high voltage power-on and the radiation-on. In one embodiment, about two seconds are provided between the high voltage power on signal and the application or generation of x-ray. Other relative timings are possible.

The low dose circuit 22 also generates a trigger signal after x-ray radiation is turned-off using the AND gate 44 and the delay generator and monostable multi-vibrator 46. When the radiation is turned off and the low dose mode is enabled by the controller 20, the AND gate 44 generates a high or activation signal to the delay generator and monostable multi-vibrator 46. A high to low transition of the radiation on signal indicating radiation-off is used to trigger the delay generator and monostable multi-vibrator 46. The delay generator and monostable multi-vibrator 46 comprises two monostable multi-vibrators, but other devices may be used. In response to an activation signal, a delay is implemented prior to latching out a monostable trigger signal to the OR gate 48. For example, resistors and capacitor values are selected for implementing a 1.5 millisecond delay, but other delays may be used including no delay. The delay compensates for phosphor persistence of the scentilator screen.

The OR gate 48 receives trigger signals from either the monostable multi-vibrator 42 responsive to the high voltage power-on signal or the delay generator and monostable multi-vibrator 46 responsive to the radiation-on and off signal. The OR gate 48 passes the trigger signals to the OR gate 26.

FIG. 3 shows the interface 14 with a modification to the low dose circuit 22 for creating two or more trigger signals after the radiation is turned-off. The delay generator and monostable multi-vibrator 46 enables a high output by another monostable multi-vibrator 50 after a delay. This other monostable multi-vibrator 50 latches high for a pulse width of 800 milliseconds, but other pulse widths corresponding to the desired number of scans by the imaging device 16 (FIG. 1) may be provided. The output of the astable multi-vibrator 36 or another oscillating signal from another source is input with the pulse width enabling signal of the monostable multi-vibrator 50 to the AND gate 52. The AND gate 52 outputs two or more trigger signals as a function of the pulse width of enablement provided by the monostable multi-vibrator 50 and the frequency of the oscillating signal from the astable multi-vibrator 36. For example, two trigger signals are generated where the monostable multi-vibrator as a pulse width of 800 milliseconds and the astable multi-vibrator has a 350 millisecond cycle. Other relative timing relationships may be used, and other combinations of high or low enabling outputs and inputs may be used.

Referring to FIG. 2, the high dose circuit 24 receives x-ray pulse rate or pulse signals and generates synchronized trigger signals at the external scan trigger input 28. The high dose circuit dose circuit 24 includes a TTL converter and opto-coupler 54, monostable multi-vibrator 56 and an AND gate 58. Additional, different or fewer components may be used. The high dose circuit 24 generates trigger signals while x-rays are generated by the x-ray source 12. The x-ray pulse rate signals are provided only when x-ray radiation is generated. Alternatively, the radiation-on signal is provided to the high dose circuit 24 for enabling generation of trigger signals substantially continuously during application of therapeutic x-rays. Any signal, such as pulse-I, or dose signals 1 or 2 of the x-ray source 12 indicating pulse timing may be used.

The TTL converter 54 converts the signals into a TTL level logic high or low signals. The opto-coupler 54 isolates the high dose circuit 24 from the x-ray source 12.

In response to the beginning of a pulse or a change to a high or low voltage of the pulse rate signal, the monostable multi-vibrator generates a trigger signal. The pulse width of the monostable multi-vibrator 56 and associated trigger signal is 30–40 microseconds, but greater or lesser pulse widths may be used. Other relative timings may be used.

The AND gate 58 is enabled by the controller 20. Where the high dose mode is active and the monostable multi-vibrator 56 generates a trigger signal, the AND gate 58 passes the trigger signal to the OR gate 26. The OR gate 26 passes the trigger signal to the external scan trigger input 28. The trigger signal is synchronized with the pulses of the x-ray source 12. Accordingly, pulse variations of the x-ray source 12 occur at a same time for each scan. A linear artifact at the same line or lines within each scan is generated due to the synchronization of the pulses with the scan.

The multi-vibrators of the interface 14 comprise latches or other logic circuits and associated resistors, variable resistors, capacitors and inductors form controlling the timing of operation of the latch circuit. Inverters and high or low voltage activation of any of the various components may be used. In an alternative embodiment, an application specific integrated circuit, processor, analog components or both analog and digital components may be used for implementing one or more components of the interface device 14.

Figure 4:
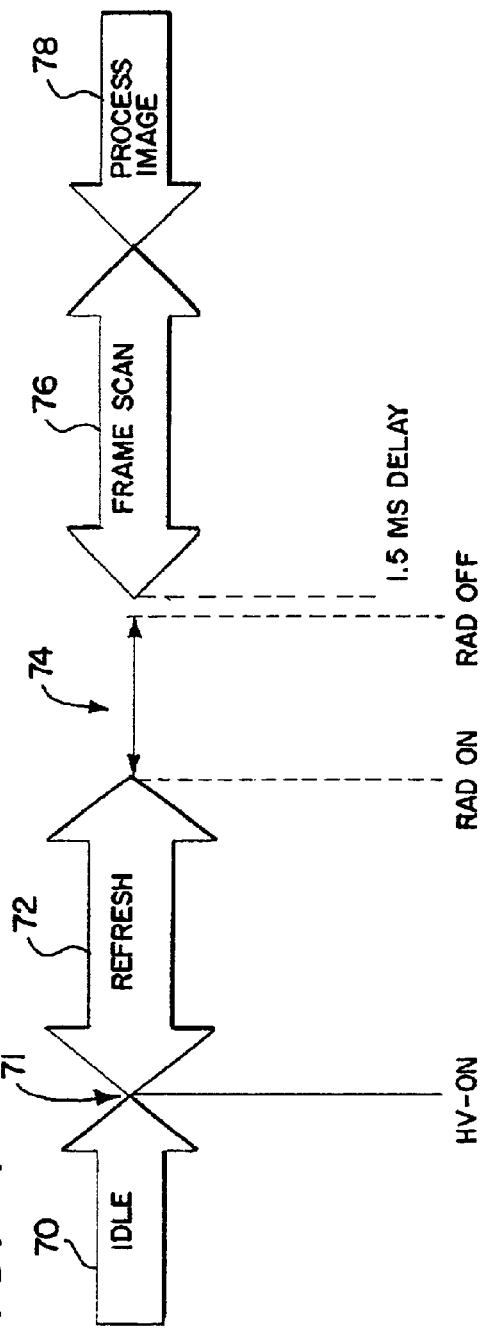
FIG. 4 is a timing diagram of one embodiment representing operation of an x-ray therapy system in a low dose mode.

FIG. 4 shows a timing diagram for the low dosage x-ray or position imaging operation of the x-ray therapy system 10. The delivered x-ray doses are at a lower dose for patient positioning or IMRT treatment. The system 10 is idle at time period 70. In response to user control, the high voltage power of the x-ray source 12 is turned on at time 71. In response, the x-ray source 12 generates a high voltage power-on output signal. The interface 14 generates 1 or more trigger signals provided to the imaging device 16 during the refresh time period 72. In response to the trigger signals, the imaging device 16 scans the active matrix to refresh or reset the imaging device 16. Immediately after or after a delay from the refresh time period 72, the x-ray source 12 generates x-ray radiation during time period 74. The x-ray radiation is generated a set time after the high voltage power is turned-on or in response to a refresh completion signal from the imaging device 16 or interface 14.

When the x-ray source 12 ceases generation of x-ray radiation, the radiation-on signal is turned off or a radiation-off signal is turned on. The interface 14 generates a trigger signal after a 1.5 millisecond delay or other delay from the radiation being turned-off. Regardless of the signal used to initiate the delay, the delay delays generation of a trigger signal after the radiation is off to compensate for scintillator screen persistence. Since scanning by the imaging device 16 is avoided during application of the radiation, the imaging device 16 integrates the light signals generated by the scintillator screen during the entire exposure time 74. At the end of the delay, the interface 14 generates one or more scan trigger signals. During the imaging time period 76, the imaging device 16 initiates and completes one or more scans or frame readouts. By avoiding frame readouts during application of x-ray radiation and due to the integration of x-ray energy by the photodiodes, good signal to noise ratio and minimal linear accelerator pulsing artifacts appear on the resulting image. Other relative time periods and modes of operation for the low dose mode may be used.

For IMRT or other multi-position x-ray therapy, multiple frames of information associated with multiple positions of the x-ray source 12 are acquired. Where larger intervals of time are provided between each treatment, additional frames of information may be scanned after each application of radiation. The characteristics of the imaging device and associated active matrix may limit the number of scans performed between application of x-rays from different positions.

During processing time period 78, the information scanned is processed. The imaging device 16 applies offset corrections, gain is corrected as a function of pixels to homogenize different pixel sensitivities and a mean or pixel correction provides software correction of defective pixels. The gain correction data for the low dose mode is acquired in a free running mode of the imaging device 16 where the imaging device 16 continuously generates frames (e.g. 50–100 frames) of information according to a programmed time not synchronized with the x-ray source 12 and with radiation but no patient. The offset correction data is acquired as an average of frames (e.g. 100 frames) where no radiation is transmitted. The offset correction frame is used to account for dark current or bias current of transistors used in the active matrix where no x-ray radiation or associated light is detected by a particular transistor or photo-detector. If more than one frame is scanned during period 76, these frames are averaged at time 78. Different, fewer or additional image processing may be provided. The resulting image is used for analysis, such as to verify a position of a patient for application of therapeutic x-rays.

Figure 5:
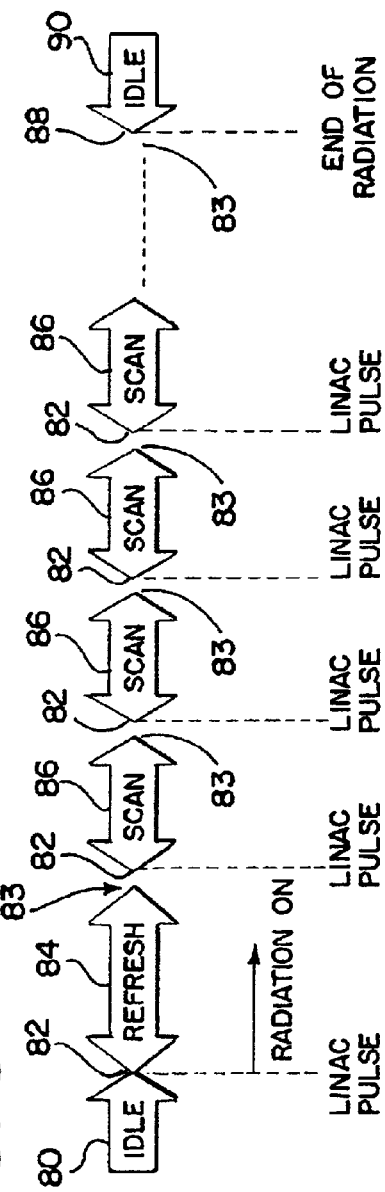
FIG. 5 is a timing diagram of one embodiment representing operation of an x-ray therapy system in a high dose or continuous scan mode.

FIG. 5 shows a timing chart representing one embodiment of operation of the x-ray therapy system 10 in a high dose mode of operation for continuous scanning while applying x-rays. The x-ray source 12 generates a high dosage x-ray radiation for therapy. Substantially continuous imaging while radiation is being applied allows for measurement of the amount of radiation dosage and effects of therapy. The x-ray source 12 and associated pulse rate output signal are idle during time period 80. At time period 82, the x-ray source 12 generates radiation for therapeutic application. A linear accelerator pulse signal is output at time 82. In response to the first pulse signal, a trigger signal is generated for refreshing the imaging device 16 during time period 84. The imaging device 16 discards or ignores the first frame which is the refresh frame and displays the subsequent frames. The refresh period 84 is the same time as scanning periods 86, but may be different. After the refresh time period 84 is complete, no or some delay represented at 83 is provided until the next pulse rate signal or linear accelerate pulse signal is output by the x-ray device 12 as represented at 82. In one embodiment, the linear accelerator pulse rate is every 5 milliseconds. The refresh time period 84 is 342.5 milliseconds, but other time periods may be used. FIG. 5 only represents linear accelerator pulses or the pulse rate signals 82 used for synchronization.

After the refresh period 84 and any associated delay 83, image scanning is triggered in response to the next pulse rate signal 82. The imaging device 16 scans to acquire image information for one two-dimensional frame of data during the scan period 86. After the scan is complete, no or some time period 83 occurs before the next pulse 82 in application of the x-ray radiation.

While the radiation is applied and continues to pulse, a plurality of scans of image data are synchronized with the linear accelerator pulses as represented by the pulse trigger at 82, the scan period at 86 and any associated delay after scan at 83. Based on the synchronization with the pulses of the x-ray source 12, linear intensity artifacts are generated in each of the scans. The linear intensity artifacts occur at a same position within each scan as a function of the synchronization. For example, where a scan period 86 occurs over a 300 millisecond time period and the x-ray source pulses the x-ray radiation at a 5 millisecond time period, approximately 60 lines within each scanned image are associated with pulsing artifacts. The pulsing artifacts occur at a same location in each image. In one embodiment, the linear artifacts occur at a same linear horizontal positions spaced evenly in each two-dimensional representation frame of data. The scan period 86 is triggered to begin at the beginning of each or a subset of the x-ray linear accelerator pulses 82. The trigger pulses generated by the high dose circuit 24 have a width of approximately 30–40, microseconds, but other timing is possible.

The imaging device 16 removes the pulse artifact from the acquired image by linking to a gain correction image acquired in a continuous scan mode. The gain correction image is a previously acquired average of one or more frames (e.g. 100 frames) corresponding to synchronized continuous scan with application of x-ray radiation without a patient being present. Both pixel sensitivity differences and linear intensity artifacts are present in the gain correction image. The averaged gain correction image is used to determine amplitude adjustment as a function of pixel and line to homogenize or equalize the pixel values of the gain correction image. An intensity change due to linear intensity artifacts is determined. The determined homogenization function or amplitude adjustments are applied to frames of data acquired in the high dose mode. Data representing lines within the two-dimensional region associated with the artifact is reduced to remove the linear intensity artifacts. Alternatively, data associated with lines of the two-dimensional region free of the artifact are increased. In yet another alternative embodiment, data associated with artifacts is decreased and data associated with no artifact is increased.

In one embodiment, two or more images acquired during the high dose scan mode are combined by summing, averaging or other filtering. Due to the synchronization, the resulting combined image data is associated with pulsing artifacts in the same linear or one-dimensional locations. Gain correction is applied to remove the pulsing linear artifact. Combining a large number of frames of data during the gain correction process also reduces the effect of dosage rate variations on the acquired images. For example, the dosage rate of the x-ray source 12 varies independently of the pulses for about the first two seconds of application of the radiation. Combining a greater number of images associated with scanning before and after the two second dosage variation increases accuracy of gain correction. For example, a 1% deviation due to dose rate variation for 50 MU exposure is provided. For dosage exposure greater than 50 MU, the accuracy may be increased further.

The image data is used for accurate dosimetric measurement. Given the reduced of artifacts due to dosage variation and pulsing rate variations and the linear response of the imaging device to applied x-rays, accurate dosimetric measurements are provided, such as amount of x-ray radiation applied or x-ray application area.

While the invention has been described above by reference to various embodiments, it should be understood that many changes and modifications can be made without departing from the scope of the invention. For example, different output signals, interface devices and trigger signals can be used for synchronizing the imaging device with the x-ray source.

It is therefore intended that the foregoing detailed description be understood as an illustration of the presently preferred embodiment of the invention, and not as a definition of the invention. It is only the following claims, including all equivalents, that are intended to define the scope of this invention.

What is claimed is:

1. An x-ray therapy system for artifact reduction, the system comprising:

an x-ray source having a data output responsive to an x-ray pulse rate, the data output separate from an x-ray output; and an imaging device responsive to x-rays from the x-ray source, the imaging device having a scan trigger input connected with the data output.

2. The system of claim 1 wherein the imaging device comprises a trigger input responsive to a trigger signal synchronized with the x-ray pulse rate.

3. The system of claim 1 further comprising a controller, a trigger signal provided to the scan trigger input responsive to a mode signal from the controller, the mode signal indicating one of a low dose mode and a high dose mode, the high dose corresponding to imaging device scanning synchronized with x-ray pulses and the low dose mode corresponding to scanning after the x-ray source ceases an output of x-rays.

4. The system of claim 1 wherein the imaging device comprises a two-dimensional array of photo-detectors and a display.

5. The system of claim 1 wherein the x-ray source comprises a megavoltage linear accelerator.

6. The system of claim 1 further comprising an interface circuit connected between the output and the scan trigger input.

7. The system of claim 6 wherein the interface circuit comprises digital logic operable to generate trigger signals for the imaging device scan trigger input as a function of a x-ray pulse signal, the trigger signals synchronized with x-ray pulses.

8. A method for artifact reduction in an x-ray therapy system, the method comprising:

(a) generating a sequence of dosage x-ray pulses and a signal with an x-ray machine;

(b) imaging in response to the dosage x-ray pulses during (a); and (c) synchronizing (b) with the dosage x-ray pulses as a function of the signal being input to an imaging device;

(d) identifying a linear artifact; and (e) gain correcting images of (b) as a function of a one-dimensional line associated with the linear artifact.

9. A method for artifact reduction in an x-ray therapy system, the method comprising:

(a) generating an image with linear pulse intensity artifacts; and (b) gain correcting the image as a function of a line with a gain correction image, the line associated with the linear pulse artifact.

10. The method of claim 9 wherein (a) comprises synchronizing scanning of a two-dimensional panel with x-ray pulses.

11. The method of claim 9 wherein (b) comprises increasing a gain of image lines free of the linear pulse artifacts.

12. The method of claim 9 wherein (b) comprises decreasing a gain of image lines corresponding to linear pulse artifacts.

13. The method of claim 9 wherein (a) comprises generating the image from a plurality of other images.

14. The method of claim 9 further comprising:

(c) measuring a quantity from data corresponding to the image.

* * * * *